United States Patent [19]

Lewis

[11] 4,248,589

[45] Feb. 3, 1981

[54] DENTAL SYRINGE WITH QUICK DISCONNECT TIP

[75] Inventor: John W. Lewis, Newberg, Oreg.

[73] Assignee: A-DEC, Inc., Newberg, Oreg.

[21] Appl. No.: 974,366

[22] Filed: Dec. 29, 1978

[51] Int. Cl.³ .............................................. A61G 17/02
[52] U.S. Cl. ...................................... 433/80; 433/126; 128/224
[58] Field of Search .................... 32/22; 128/224, 239, 128/247; 433/80, 126

[56] References Cited

U.S. PATENT DOCUMENTS

| | | | |
|---|---|---|---|
| 2,029,734 | 2/1936 | Meitzler | 128/224 |
| 3,254,646 | 6/1966 | Staunt | 128/224 |
| 4,026,025 | 5/1977 | Hunt | 32/22 |
| 4,149,315 | 4/1979 | Page, Jr. et al. | 32/22 |

*Primary Examiner*—F. Barry Shay
*Assistant Examiner*—John J. Wilson

*Attorney, Agent, or Firm*—Klarquist, Sparkman, Campbell, Leigh, Hall & Whinston

[57] ABSTRACT

The specification discloses a dental syringe having a head, a tip and a releasable coupling mounted on the head. The head and tip have a corresponding number of fluid passages therethrough. The coupling includes a cylindrical base and a lock nut which screws over the base. The base and the lock nut define an axially extending bore which communicates with the passages through the head and removably receives the rearward portion of the tip. An elastomeric O-ring is positioned between the base and the lock nut and surrounds the bore. When the rearward portion of the tip is fully inserted in the bore the O-ring seats in a groove surrounding the rearward portion of the tip. When the lock nut is fully screwed over the base, deformation of the O-ring is substantially prevented and the tip cannot be withdrawn or ejected from the coupling.

3 Claims, 3 Drawing Figures

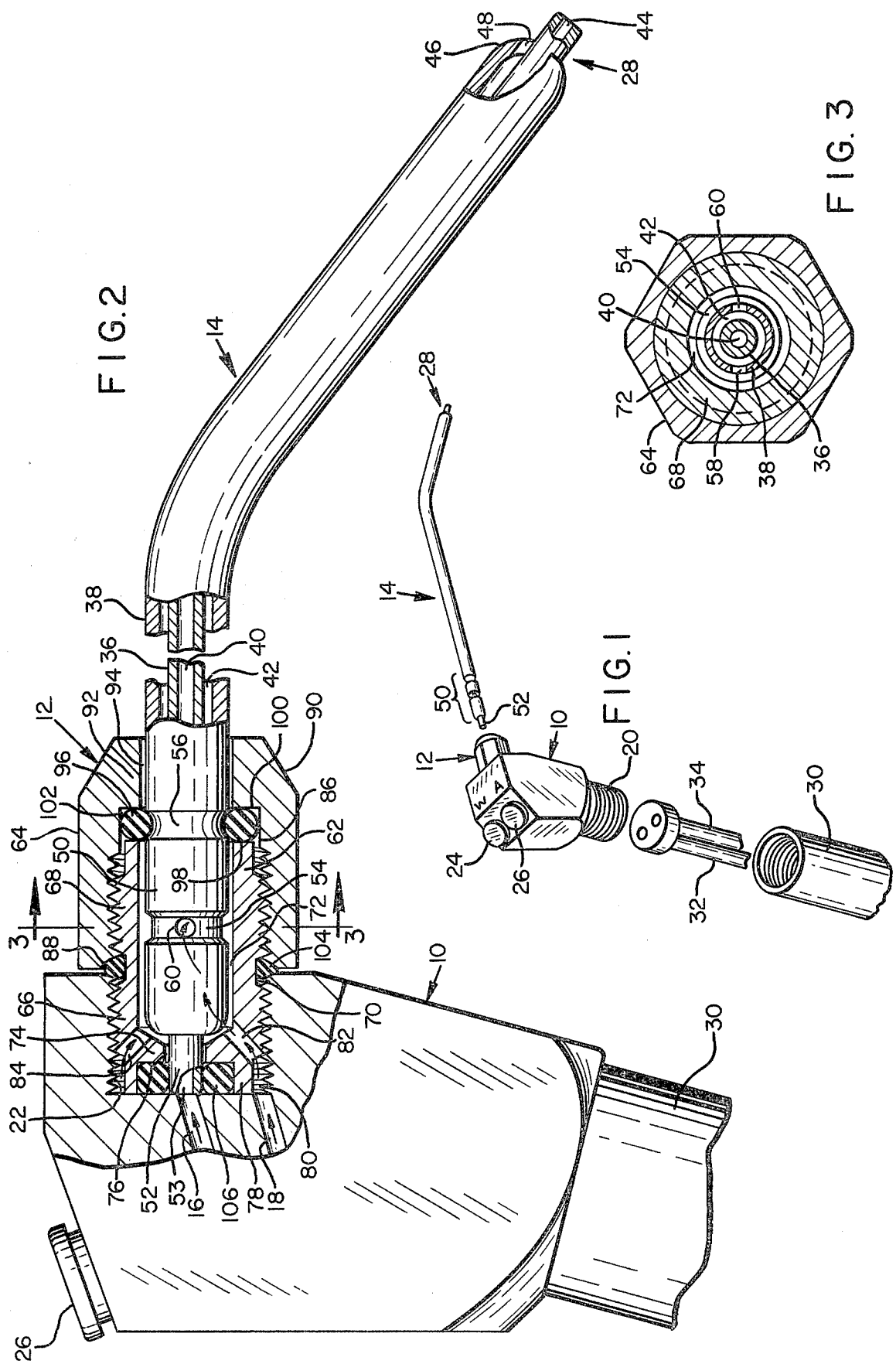

DENTAL SYRINGE WITH QUICK DISCONNECT TIP

BACKGROUND OF THE INVENTION

The present invention relates to dental syringes, and more particularly to a dental syringe adapted to permit its tip to be quickly inserted and withdrawn from its head.

Dental syringes are widely used by dentists, dental hygenists, dental assistants and the like. They are hand-held instruments which deliver water and air under pressure into a patient's mouth for washing and drying purposes. One such dental syringe is disclosed in U.S. Pat. No. 3,698,088. It includes a head which is coupled to supply hoses and an elongate tip which is coupled to the head and is inserted into the patient's mouth. The hoses supply water at about 40 PSI and air at about 80 PSI. Valves in the head are selectively hand operated to discharge water or air through the distal end of the tip.

Cross contamination is one of the principal problems encountered with dental syringes. Bacteria and viruses can be communicated from patient to patient unless the syringe tip is adequately sanitized. The safest and most desirable approach is to remove the syringe tip from the head and autoclave it after each patient treatment. In addition, it is desirable to be able to replace worn tips or change to tips of different configurations quickly and easily.

However, the tips of dental syringes heretofore known have not been readily removable from the syringe heads. Frequently such removal has necessitated the unscrewing of a coupling from the head and the sliding of the coupling off of the tip which has made it necessary for the coupling to be autoclaved also. The tip and coupling usually have a number of small elastomeric O-rings which must be removed before autoclaving because they cannot endure heat and pressure without being damaged. The removal and replacement of these small O-rings has been a time consuming, exasperating experience.

Therefore, it is desirable to have a dental syringe adapted to permit its tip to be quickly inserted and withdrawn from its head. However, when the tip is inserted it must be firmly held, so as not to become accidentally disengaged.

SUMMARY OF THE INVENTION

It is an object of the present invention to provide a dental syringe adapted to permit its tip to be quickly inserted and withdrawn from its head.

It is another object of the present invention to provide a releasable coupling for a dental syringe that will firmly hold its tip while still allowing for rapid removal and replacement of the tip.

It is a further object of the present invention to provide a dental syringe tip adapted to be quickly disconnected from the syringe head and autoclaved without requiring the removal and replacement of O-rings.

The present invention provides a dental syringe having a head, a tip, and coupling means. The head and the tip each have a fluid passage therethrough. The coupling means is mounted on the head and releasably holds the tip so that fluid can flow from the passage through the head into the passage through the tip. The coupling means is actuable to permit the tip to be inserted and withdrawn from the coupling means without removing the coupling means from the head. The coupling means is further actuable to prevent the tip from being withdrawn from the coupling means after the tip has been inserted into the coupling means.

BRIEF DESCRIPTION OF THE DRAWINGS

FIG. 1 is an exploded isometric view of one embodiment of the dental syringe of the present invention showing its tip withdrawn;

FIG. 2 is an enlarged side elevational view of the dental syringe of FIG. 1 with portions broken away; and FIG. 3 is a sectional view taken along line 3—3 of FIG. 2.

DESCRIPTION OF THE PREFERRED EMBODIMENT

Referring to FIG. 1, the illustrated embodiment of a dental syringe constructed in accordance with the present invention includes a head 10, a coupling 12, and a tip 14. The head 10 has internal water and air passages 16 and 18 (FIG. 2) which extend from the end of an externally threaded shank 20 at the bottom of the head (FIG. 1) to an internally threaded cylindrical cavity 22 (FIG. 2) in the top frontal surface of the head. The water passage 16 opens in the center of the bottom of the cavity 22. The air passage 18 opens in the bottom of the cavity 22 adjacent its sidewall.

Push buttons 24 and 26 (FIG. 1) on the top rear surface of the head are coupled to conventional normally closed valves mounted internally of the head (not shown) and are selectively hand-operated in order to discharge water, air, or both through the distal end 28 of the tip 14. A handle 30 can be threadedly engaged with the shank 20 in order to connect water and air supply hoses 32 and 34 to the water and air passages 16 and 18, respectively.

The tip 14 (FIG. 2) comprises inner and outer elongate, coaxial, spaced apart pipes 36 and 38 which define water and air passages 40 and 42, respectively. The forward portions of the pipes are angled with respect to the rearward portions. The forward end 44 of the inner pipe 36 is open and the forward end 46 of the outer pipe 38 is bent inwardly and is sealed to the inner pipe 36. The forward end 46 has a plurality of annularly spaced nozzle apertures such as 48. When the push buttons 24 and 26 are simultaneously depressed an atomized water spray is produced.

The rearward portion 50 of the outer pipe 38 terminates short of the rearward portion 52 of the inner pipe 36 and is bent inwardly and sealed to the rearward portion 52. The rearward end 53 of the inner pipe 36 is open and coaxial with the water passage 16 and abuts the bottom of the cavity 22 when inserted in the coupling 12. The periphery of the rearward portion 50 is formed with a pair of axially spaced, rearward and forward annular grooves 54 and 56. A pair of diametrically positioned inlet apertures 58 and 60 (FIG. 3) extend through the wall of the outer pipe 38 in the groove 54.

Referring to FIG. 2, the coupling 12 includes a cylindrical base 62 and a cylindrical lock nut 64. The base 62 has an externally threaded rearward portion 66 which is screwed into the cavity 22 in the head 10. The base 62 has an externally threaded forward portion 68 which is separated from the rearward base portion 66 by an annular groove 70. The base 62 has an axially extending bore 72 which has a diameter slightly larger than the outside diameter of the outer pipe 38 so that it can removably receive the rearward portion of the tip 14 and provide passage for air.

An annular flange 74 extends radially inwardly from the rearward base portion 66 and defines a hole 76 which removably receives the rearward portion 52 of the inner pipe 36. Another annular flange 78, having a smaller outside diameter than the inside diameter of the cavity 22, extends axially from the rearward base portion 66. The flange 78 defines an annular chamber 80 between the flange 78 and the sidewall of the cavity 22 which communicates with the air passage 18.

Ducts 82 and 84 in the base 62 extend from the bore 72 in the base to the chamber 80. When the rearward portion of the tip is fully inserted in the bore 72, air can flow from the air passage 18 into the chamber 80, through the ducts 82 and 84, into the bore 72, through the apertures 58 and 60, into the air passage 42 and through the tip.

The lock nut 64 has an annular inner wall 86, the rearward portion of which has internal threads corresponding to the external threads on the forward base portion 68. The lock nut 64 is screwed over the forward base portion 68. The rearward end of the lock nut 64 is formed with a beveled surface 88 on its inner portion. The tapered forward end 90 of the lock nut 64 is formed with an annular portion 92 which extends radially inwardly and defines an axially extending bore 94 with a diameter slightly larger than the outside diameter of the outer pipe 38. The bore 94 removably receives the rearward portion of the tip 14. The bores 94 and 72 are aligned and form a single continuous bore so that the tip can be fully inserted and withdrawn from the coupling 12.

A resilient washer or O-ring 96 is positioned between the forward end 98 of the base 62 and the shoulder 100 defined by the annular nut portion 92. The O-ring 96 is made of an elastomeric compound. O-rings made of Nitrile Buna N are suitable. They are commercially available in a wide variety of sizes. When the O-ring 96 is not deformed, i.e. when it is not in the coupling 12 and not surrounding the tip 14, it has an inside diameter which is slightly less than the minimum outside diameter of the outer pipe 38 in the forward groove 56. It has an outside diameter which is slightly greater than the inside diameter of the cylindrical cavity defined by the unthreaded forward portion of the inner wall 86 of the lock nut 64.

In FIG. 2, the rearward portion of the tip 14 is shown fully inserted in the bores 72 ad 94 of the coupling 12. The lock nut 64 is fully screwed over the forward base portion 68, i.e. the rearward end of the nut is adjacent the surface of the head 10. The O-ring 96 is encased in an annular groove 102 defined by the forward base end 98, the inner nut wall 86 and the nut shoulder 100. The O-ring 96 surrounds the bore in the coupling and is seated in the forward groove 56 surrounding the rearward portion of the tip 14. When the lock nut 64 is fully screwed over the forward base portion 68, the O-ring 96 is substantially confined in the groove 102 and cannot deform sufficiently to increase its inside diameter enough to permit the tip to be withdrawn or ejected from the coupling. Withdrawal or ejection of the tip 14 from the coupling 12 is now substantially impossible without physically destroying the O-ring 96. This would require forces substantially greater than those generated by manually pulling on the tip or resulting when the tip becomes plugged. However, the tip 14 can still be manually rotated so that its angled forward portion will be conveniently positioned for retracting the lip, tongue, etc. or projecting air or water where desired. The O-ring 96 also prevents air from escaping from the bore 72.

The couplng 12 may be actuated to release the tip 14 by untightening the lock nut 64, i.e. partially unscrewing the lock nut a predetermined amount so that the O-ring 96 can deform sufficiently to allow the tip to be fully withdrawn. The groove 102 will enlarge and permit the inside diameter of the O-ring 96 to enlarge by deforming so that its axial width increases. When the lock nut 64 is partially unscrewed in this manner, the tip 14 can be readily withdrawn and replaced. The O-ring 96 will remain in position in the coupling 12. The tip 14 has no O-rings connected thereto and it may be directly placed into an autoclave for sterilization.

Since the inside diameter of the O-ring 96 (when not deformed) is slightly smaller than the minimum outside diameter of the outer pipe 38 in the groove 56 there will be some resistance encountered each time the tip 14 is inserted and withdrawn from the coupling 12. This is because the O-ring 96 grips the tip 14 as it slides over the same. However, the resistance is only minimal and does not inhibit the rapid replacement of tips.

A resilient washer or O-ring 104 which is also made of an elastomeric compound such as Nitrile Buna N is positioned in the groove 70 surrounding the base 62. The O-ring 104 is deformed between the beveled surface 88 of the lock nut 64, the surface of the groove 70, and the surface of the head 10 when the lock nut is fully screwed over the forward base portion 68. The O-ring 104 prevents air from escaping from the coupling 12 by flowing from the chamber 80, between the engaged external and internal threads of the rearward base portion 66 and the cavity 22, and between the lock nut rearward end and the head 10. It also prevents air from escaping from the coupling 12 by flowing from the groove 102, between the engaged external and internal threads of the forward base portion 68 and the lock nut 64, and between the lock nut rearward end and the head 10.

A resilient washing or O-ring 106 which is also made of an elastomeric compound such as Nitrile Buna N, is positioned within the axially extending flange 78 and surrounds the rearward portion 52 of the inner pipe 36. It is deformed between the radially extending flange 74 and the bottom of the cavity 22 when the rearward base portion 66 is fully screwed into the cavity 22. The O-ring 106 seals the connection between the water passages 16 and 40. It prevents water from leaking into the chamber 80 by flowing between the rearward end of the flange 78 and the bottom of the cavity 22. It also prevents water from flowing into the bore 72 by flowing through the hole 76.

Having described a preferred embodiment of the present invention, it is apparent that the invention permits of modification in arrangement and detail. For example, the coupling can be modified so that the O-ring 96 deforms into the forward groove 56 upon tightening of the lock nut 64 and thereafter recedes out of the groove when the lock nut is untightened. The forward groove 56 can be eliminated and the coupling can be modified so that the O-ring 96 will grip the tip firmly enough, upon tightening of the lock nut 64, to prevent ejection of the tip. However, such modifications, as well as others, which will be apparent, are within the spirit and scope of the present invention.

What is claimed is:
1. In a dental syringe,
a head having a fluid passage therethrough,
a tip having a fluid passage therethrough,
coupling means mounted on the head for releasably holding the tip so that fluid can flow from the passage through the head into the passage through the tip,
the coupling means actuable to permit the tip to be inserted and withdrawn from the coupling means without removing the coupling means from the head and further actuable to prevent the tip from being withdrawn from the coupling means after the tip has been inserted into the coupling means,
means for preventing fluid from escaping from the coupling means other than through the tip,
the coupling means including
a base mounted on the head,
a lock nut screwed over the base,
the base and lock nut defining a bore for removably receiving the rearward portion of the tip,
resilient means positioned between the base and lock nut and surrounding the tip,
the resilient means being adapted to prevent the tip from being withdrawn from the bore when the lock nut is screwed a predetermined amount over the base,
the periphery of the rearward portion of the tip having an annular groove,
the resilient means comprising an elastomeric O-ring which is seated in the groove when the rearward portion of the tip is inserted in the bore,
the base and the lock nut preventing sufficient deformation of the O-ring to permit the tip to be withdrawn from the bore when the lock nut is screwed the predetermined amount over the base so that the tip is positively held against withdrawal from the bore while permitting rotation of the tip without loosening of the lock nut, and so that said O-ring forms a fluid tight seal between the base, lock nut, and tip.

2. The dental syringe of claim 1 including
means for preventing fluid from escaping from the coupling means other than through the tip including a first elastomeric O-ring surrounding the base and deformed between the lock nut and the head when the lock nut is screwed the predetermined amount over the base, and
a second elastomeric O-ring surrounding the rearward portion of the tip and deformed between the base and the head.

3. In a dental syringe,
a head having a first water passage and a first air passage extending therethrough and an internally threaded cylindrical cavity in its surface having a bottom and a sidewall, the first water passage opening in the center of the bottom and the first air passage opening in the bottom adjacent the sidewall,
a tip having inner and outer elongate, coaxial, spaced apart pipes, the inner pipe defining a second water passage and the outer pipe defining a second air passage, the forward ends of the pipes having discharge openings, the rearward portion of the outer pipe terminating short of and sealed to the rearward portion of the inner pipe and having axially spaced rearward and forward annular grooves, the rearward portion of the outer pipe further having an aperture therethrough in the rearward groove, and the rearward end of the inner pipe having an opening,
a coupling having an externally threaded cylindrical base, the rearward portion of the base screwed into the cavity in the head, and an internally threaded cylindrical lock nut screwed over the forward portion of the base, the base and nut defining an axially extending bore therethrough adapted slidably to receive the rearward portion of the tip, the base having a first annular flange which extends radially inwardly from the rearward portion of the base and defines a hole which receives the rearward portion of the inner pipe so that the first and second water passages mate, the base further having a second annular flange which extends axially from the rearward portion of the base and defines a chamber between the second flange and the sidewall, the chamber communicating with the first air passage, and the base further having a duct extending between the bore and the chamber,
a first elastomeric O-ring positioned between the base and the nut and seated in the forward groove when the rearward portion of the tip is fully inserted in the bore, the base and the nut confining the first O-ring and preventing sufficient deformation thereof to permit the tip to be slidably withdrawn from the bore when the nut is fully screwed over the base,
a second elastomeric O-ring surrounding the base and deformed between the nut and the head when the nut is fully screwed over the base,
a third elastomeric O-ring surrounding the rearward portion of the inner pipe and deformed between the first flange and the head,
whereby when the nut is partially screwed off of the base, the rearward portion of the tip may be manually inserted and withdrawn from the coupling, and when the rearward portion of the tip is fully inserted in the coupling and the nut is fully screwed over the base the first O-ring will prevent withdrawal or ejection of the tip, and the first, second, and third O-rings will prevent water or air from escaping from the coupling except through the tip.

* * * * *